United States Patent
Li

(10) Patent No.: US 9,506,902 B2
(45) Date of Patent: Nov. 29, 2016

(54) METHODS FOR THE DETECTION OF SPOILAGE OF OILS

(71) Applicants: NUTRASOURCE DIAGNOSTICS INC., Guelph (CA); NORDIC NATURALS, INC., Watsonville, CA (US)

(72) Inventor: Lianghong Li, Mississauga (CA)

(73) Assignees: NUTRASOURCE DIAGNOSTICS INC., Guelph, Ontario (CA); NORDIC NATURALS, INC., Watsonville, CA (US)

( * ) Notice: Subject to any disclaimer, the term of this patent is extended or adjusted under 35 U.S.C. 154(b) by 0 days.

(21) Appl. No.: 14/891,794

(22) PCT Filed: May 16, 2014

(86) PCT No.: PCT/CA2014/000431
§ 371 (c)(1),
(2) Date: Nov. 17, 2015

(87) PCT Pub. No.: WO2014/183202
PCT Pub. Date: Nov. 20, 2014

(65) Prior Publication Data
US 2016/0146771 A1 May 26, 2016

Related U.S. Application Data

(60) Provisional application No. 61/824,878, filed on May 17, 2013.

(51) Int. Cl.
*G01N 33/03* (2006.01)
*G01N 30/06* (2006.01)
*A23D 9/00* (2006.01)
*C11C 3/00* (2006.01)
*G01N 30/02* (2006.01)

(52) U.S. Cl.
CPC .............. *G01N 33/03* (2013.01); *G01N 30/06* (2013.01); *C11C 3/006* (2013.01); *G01N 2030/027* (2013.01)

(58) Field of Classification Search
CPC . G01N 30/06; G01N 33/03; G01N 2030/027
See application file for complete search history.

(56) References Cited

U.S. PATENT DOCUMENTS

2015/0223483 A1* 8/2015 Syed ...................... A23D 9/007
426/545

OTHER PUBLICATIONS

Steele, E. (ed). "Understanding and Measuring the Shelf-Life of Food" Woodhead Publishing Ltd. Boca Raton. 2004. p. 136. Retrieved from Google Books on Jul. 9, 2014, http://books.google.ca/books?id+bdnfe_Q5UAMC&lpg=PAL136#v=onepage&q&f=true.

* cited by examiner

Primary Examiner — Jennifer Wecker

(57) ABSTRACT

Methods for the detection of spoilage of oils containing unsaturated fatty acids is disclosed. Specific methods include the determination of p-anisidine in oils containing unsaturated fatty acids using high performance liquid chromatography after p-anisidine is added to the oil containing unsaturated fatty acids, and allowed to react with oxidation products.

22 Claims, No Drawings

METHODS FOR THE DETECTION OF SPOILAGE OF OILS

FIELD OF THE INVENTION

Provided herein are methods for the detection of spoilage of oils containing unsaturated fatty acids. Also provided herein are methods for the detection of spoilage in oil containing unsaturated fatty acids by measuring p-anisidine remaining after an addition of a known amount of p-anisidine to the oil, using high performance liquid chromatography.

BACKGROUND OF THE INVENTION

Oils containing unsaturated fatty acids are used in a variety of food, health and medical applications, such as dietary supplements. Oils containing unsaturated fatty acids can come from a variety of sources, for example, vegetable oils, animal oils and marine oils. Marine oils (e.g. fish oils) comprising omega-3 polyunsaturated fatty acids, in particular, are used in a variety of dietary/therapeutic compositions.

Oils containing unsaturated fatty acids tend to spoil upon storage by oxidation processes. See e.g., Shahidi et al. in BAILEY'S INDUSTRIAL OIL AND FAT PRODUCTS (2005, 6th Ed., Fereidoon Shahidi, ed.), Chapter 8, pages 357-385 . As the oxidation proceeds, various oxidation products are produced that can make the oil unfit for use in health and nutritional applications. When a certain level of these oxidation products is reached, making the oil unfit for use in health and nutritional applications, the oil is spoiled or rancid. Primary oxidation products are hydroperoxides that are relatively unstable and susceptible to further decomposition. Secondary oxidation products thought to be produced from the further reaction of the hydroperoxides include aldehydes, ketones, alcohols, hydrocarbons, volatile organic acids, and epoxy compounds, among others. See id., at 357-359. The oxidation level of oil may be measured by a number of methods, including the measurement of the iodine and peroxide values by titration methods; and the measurement of conjugated dienes and trienes, 2-thiobarbituric acid value, p-anisidine value, and carbonyl value by spectrophotometric methods. See id.

The p-anisidine value is a common method for measuring secondary oxidation products via a "p-anisidine value" or "anisidine value" using the "p-anisidine test." See e.g., Shahidi at 368. For example, in evaluating oxidation of salad oils, a study found a high correlation between the anisidine value and flavor scores of the salad oils. See Gray et al., *J. Am. Oil Chem. Soc.*, vol. 55, p. 539-545 (1978). The reaction of p-anisidine with secondary oxidation products, which include unsaturated aldehydes and ketones, produces yellowish products that absorb at 350 nm. See Shahidi at 368. The method is performed using a spectrophotometer, and the anisidine value is given by multiplying the optical density by 100, of a solution of 1.00 gm oil in 100 mL solution containing p-anisidine, at a wavelength of 350 nm. See American Oil Chemists' Society Official Method Cd-18-90. Any materials in solution that absorbs at 350 nm will be included in the anisidine value, because a spectrophotometer does not discriminate between materials that absorb at the same wavelength.

Studies using instrumental methods have been employed to assess the impurities and oxidation level of oils. One such study used solid phase microextraction followed by gas-chromatography-mass spectroscopy to assess fish oils. See Ritter et al., *Lipids*, vol. 47, p. 1169-1179 (2012). This study required multiple steps and purports to detect over 100 oxidation products in samples of oxidized fish oil. See Ritter at 1173. Another study used high-performance liquid chromatography, gas-chromatography-mass spectroscopy, and $^{13}$C NMR to identify oxidation products in fish oil. See Saeed et al., *J. Am. Oil Soc. Chem.*, vol. 76, p. 391-397. This study identified numerous oxidation products in fish oil, and the chromatograms displayed a complex mixture with overlapping peaks. See Saeed at 394, Fig. 1. Additionally, a study employing Fourier Transform Infrared spectroscopy (FTIR) was used to predict the anisidine value of palm olein. This study used mixtures of oxidized and fresh palm olein to produce a calibration curve for palm olein up to an anisidine value of 17. See Man et al., *J Am. Oil Soc. Chem.*, vol. 76, p. 243-247.

All of the above instrumental methods were able to assess impurities and oxidation of oils with varying success. The chromatographic techniques (see Ritter; see Saeed) produced chromatograms with large numbers of peaks indicating many different compounds, which can make assessment of oxidation of the oil difficult. Additionally, the oxidation impurities from different oils can be different, adding complication to any analysis. The FTIR method (see Man), which according to the authors, worked well for palm olein, would most likely require individual calibration curves to be generated for each type and blend of oil that requires analysis. Thus, a more straightforward and robust method of determining an oxidation level of an oil is needed that does not involve identifying multiple impurities or include multiple calibrations.

The current method for measuring the anisidine value in oils containing unsaturated fatty acids is a simple method but is deficient, at least for the reason that the current anisidine value method produces false positives when certain additives (e.g., flavorings and colorants) are present in the oil. Additives that absorb at 350 nm will contribute to the anisidine value, and produce an anisidine value that is higher than the same oil without the additives present. This overly high value would lead to a measurement that is incorrect, and falsely indicate that the oil oxidized, and thus spoiled or rancid. Therefore, an improved, straightforward method is desired that can more accurately determine the oxidation of oils containing unsaturated fatty acids across a variety of present and future oil formulations and products that contain materials that can interfere with the existing tests.

BRIEF SUMMARY OF THE INVENTION

Provided herein are methods for the detection of spoilage in oil containing unsaturated fatty acids by determination of p-anisidine content using high performance liquid chromatography (HPLC). In certain embodiments, the oxidation level of oil containing unsaturated fatty acids is measured by quantification of p-anisidine remaining in a sample of oil by HPLC.

In one embodiment of the present disclosure, a method of determining oxidation of a sample of oil comprises adding a known amount of p-anisidine to a sample of oil, waiting a time period after the addition of the known amount of p-anisidine to the sample of oil, measuring an amount of p-anisidine remaining in the sample of oil after the time period has elapsed, and calculating a percent p-anisidine remaining wherein the percent p-anisidine remaining is a determination of oxidation of the sample of oil.

In certain embodiments, the sample of oil comprises an oil containing unsaturated fatty acids. In certain embodiments, the sample of oil comprises one or more oils selected from the group of vegetable oil, animal oil and marine oil. In certain embodiments, the sample of oil comprises marine oil. In certain embodiments, the marine oil comprises a fish oil containing omega-3 fatty acids.

In certain embodiments, the measuring of an amount of p-anisidine is done by HPLC. In certain embodiments, the percent p-anisidine remaining in the sample solution of less than 50%, 75%, 80%, 85%, 86%, 87%, 88%, 89%, 90%, 91%, 92%, 93%, 94%, or 95% is an indication of oxidation of the sample of oil in the sample solution. In certain embodiments, the determination of oxidation of the sample of oil indicates that the sample of oil is spoiled. In certain embodiments, the amount of p-anisidine remaining in the sample of oil is measured by comparing an amount of p-anisidine in the sample oil to an amount of p-anisidine in a standard p-anisidine solution.

In another embodiment of the present disclosure, a method of determining oxidation of a oil comprising an unsaturated fatty acid, comprises the steps of: preparing a standard p-anisidine solution comprising an amount of p-anisidine; preparing a sample solution comprising an amount of p-anisidine and an amount of a sample of oil, where the sample of oil comprises an unsaturated fatty acid and where the amount of p-anisidine in the sample solution before any p-anisidine reacts with the sample of oil is the same as the amount of p-anisidine in the standard p-anisidine solution; measuring the amount of p-anisidine in the standard p-anisidine solution; measuring the amount of p-anisidine in the sample solution; and calculating a percent of p-anisidine remaining in the sample solution as compared with the standard p-anisidine solution, where the percent of p-anisidine remaining in the sample solution is an indication of oxidation of the sample of oil in the sample solution.

In certain embodiments, the measuring of an amount of p-anisidine is done by chromatography. In certain embodiments, the chromatography is HPLC.

In certain embodiments, the percent p-anisidine remaining in the sample solution of less than 50%, 75%, 80%, 85%, 86%, 87%, 88%, 89%, 90%, 91%, 92%, 93%, 94%, or 95% is an indication of oxidation of the sample of oil in the sample solution.

In certain embodiments, the amount of p-anisidine in the standard p-anisidine solution is from about 0.1 mg/mL to 1 mg/mL, from about 0.1 mg/mL to 0.5 mg/mL, or from about 0.2 mg/mL to 0.3 mg/mL.

In certain embodiments, the amount of p-anisidine in the standard p-anisidine solution is about 0.2 mg/mL, about 0.25 mg/mL, about 0.3 mg/mL, about 0.4 mg/mL or about 0.5 mg/mL.

In certain embodiments, the amount of the sample of oil in the sample solution is from about 0.01 mL/mL to 0.2 mL/mL, from about 0.02 mL/mL to 0.1 mL/mL, or from about 0.05 mL/mL to 0.1 mL/mL.

In certain embodiments, the amount of the sample of oil in the sample solution is about 0.2 mL/mL, about 0.1 mL/mL, about 0.05 mL/mL, or about 0.02 mL/mL.

In certain embodiments, the measuring of the amount of p-anisidine in the sample solution is done more than 1 minute, 5 minutes, 10 minutes, 20 minutes, 30 minutes, 60 minutes, 120 minutes, 180 minutes, or more than 180 minutes after preparing the sample solution.

In certain embodiments, the measuring of the amount of p-anisidine produces a peak area, a weight, a concentration, a molar concentration, a weight concentration, or a molar ratio.

In certain embodiments, the standard p-anisidine solution and sample solution further comprise acetic acid.

In certain embodiments, the sample of oil comprises one or more oils selected from the group of vegetable oil, animal oil and marine oil. In certain embodiments, the sample of oil comprises marine oil. In certain embodiments, the marine oil comprises a fish oil containing omega-3 fatty acids.

In certain embodiments, the amount of p-anisidine in the standard p-anisidine solution is about 0.25 mg/mL. In certain embodiments, the amount of the sample of oil in the sample solution is about 0.1 mL/mL.

In certain embodiments, the sample of oil comprises an additive. In certain embodiments, the additive has a molar absorptivity at 350 nm of at least 100 $M^{-1}cm^{-1}$. In certain embodiments, the additive is a coloring agent, a flavoring agent, a preserving agent, an antioxidant, or a vitamin. In certain embodiments, a reaction product of the additive with p-anisidine has a molar absorptivity at 350 nm of at least 1000 $M^{-1}cm^{-1}$.

In certain embodiments, a ratio of the amount of p-anisidine in the sample solution to the amount of the sample of oil in the sample solution is from about 4:1 to 1:4, about 2:1 to 1:2, about 4:1 to 1:1, or about 3:1 to 2:1, wherein the ratio is volume to volume, mass to volume, volume to mass, or mass to mass.

In certain embodiments, a ratio of the amount of p-anisidine in the sample solution to the amount of the sample of oil in the sample solution is about 4:1, about 3:1, about 2.5:1, about 2:1, about 1.5:1, or about 1:1, wherein the ratio is volume to volume, mass to volume, volume to mass, or mass to mass. In certain embodiments, the ratio is 2.5:1, mass to volume.

DETAILED DESCRIPTION OF THE INVENTION

Provided herein are methods for the detection of spoilage of oil containing unsaturated fatty acids by determination of an amount of p-anisidine (4-methoxyaniline, depicted below) remaining in a sample of oil containing unsaturated fatty acids after the addition of a known amount of p-anisidine to the sample of oil.

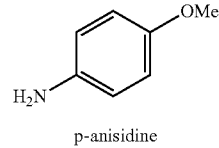

p-anisidine

Through oxidation processes, oil that contains unsaturated fatty acids can generate impurities that can cause the oil to become spoiled or rancid. Some of the impurities generated can be aldehydes and ketones. Determining an amount of aldehydes and/or ketones present in a sample of oil can give a measure of the oxidation level of the oil, and can indicate whether the oil can be considered spoiled or rancid. Certain amines, such as p-anisidine, can react with impurities, such as aldehydes and ketones, generated by oxidation in oil.

In certain embodiments, the determination of the amount of p-anisidine remaining in a sample of oil containing unsaturated fatty acids can be done using high performance liquid chromatography (HPLC). In certain embodiments, the oxidation level of oil containing unsaturated fatty acids is measured by quantification of p-anisidine in a sample of oil by HPLC. In certain embodiments, the quantification can be done by comparing the amount of p-anisidine remaining in a sample of oil to a standard p-anisidine solution with a known concentration.

In certain embodiments, the method comprises the detection of spoilage in oils containing unsaturated fatty acids and containing one or more additives, including but not limited to a flavorings, colorants, vitamins, minerals, dispersants, emulsifiers, antioxidants, surfactants, alcohols, polyols, and other materials that are generally recognized as safe. In certain embodiments, the additive can be included in the oil itself. In certain embodiments, the additive can be added to a material in contact with the oil, such as the container material, packaging or formulation forms such as capsule shells, where the additive can transfer to the oil. In certain embodiments, the additive includes compounds with a carbonyl group (>C═O), or compounds with a carbonyl group and a carbon-carbon double bond. In certain embodiments, the carbon-carbon double bond can be conjugated with the carbonyl group (i.e., an αβ-unsaturated carbonyl compound).

In certain embodiments, the method comprises the detection of spoilage in oils containing unsaturated fatty acids where the additive includes a flavoring agent, which includes, but is not limited to, a lemon flavoring.

In certain embodiments, the oil containing unsaturated fatty acids can be a vegetable oil, an animal oil, a marine oil, or an oil that can be derived from a vegetable oil, an animal oil, or a marine oil. In certain embodiments, the oil containing unsaturated fatty acid can be an edible oil. In certain embodiments, the oil containing unsaturated fatty acid can be a vegetable oil. In certain embodiments, the oil containing unsaturated fatty acid can be an animal oil. In certain embodiments, the oil containing unsaturated fatty acid can be a marine oil. In certain embodiments, the unsaturated fatty acid can be a polyunsaturated fatty acid (PUFA).

Definitions

As used herein, the term "about" means that the value or amount to which it refers can vary by ±5%, ±2%, or ±1%.

As used herein, the terms "spoil", "spoiled", "spoilage", or "rancid" can be used interchangeably, and refers to a level of oxidation of an oil that makes the oil unfit for use.

As used herein, the term "vegetable oil" refers to an oil, derivatives of an oil, or derivatives of components of an oil that originate from a plant source.

As used herein, the term "animal oil" refers to a fat or oil, derivatives of a fat or oil, derivatives of components of a fat or oil that originate from an animal organism.

As used herein, the term "marine oil" refers to an oil, derivatives of an oil, derivatives of components of an oil that originate from an organism of marine origin, and is to be interpreted broadly and comprises oils from marine organisms which include algae, plankton, krill, fish, shellfish (crustaceans) and sea mammals, including genetically manipulated/transformed organisms, as well as parts or fractions and components of such marine oils containing at least one PUFA. Marine oils can include omega-3 fatty acids as one of the PUFA. In its broadest sense the term "marine oil" comprises oils obtainable from any organism which oils may upon degradation give rise to the occurrence of aldehydes and ketones responsible for development of "fishy" or other unpleasant smell and taste. Such organisms include animals, microorganisms (e.g., yeasts) and plants as well as parts of the foregoing, e.g., seeds. In certain embodiments, a marine oil can also be an animal oil, for example, when the oil originates from a fish or sea mammal.

An oil can be considered a vegetable oil if the oil includes at least 10%, 20%, 30%, 40%, 50%, 60%, 70%, 80%, 90%, 95% or 99% or more vegetable oil derived from a plant organism, where the oil derived from a plant organism can include processes to convert the oil to derivatives of the oil and/or derivatives of the fatty acid contained in the oil.

An oil can be considered an animal oil if the oil includes at least 10%, 20%, 30%, 40%, 50%, 60%, 70%, 80%, 90%, 95% or 99% or more oil derived from an animal, where the oil derived from an animal can include processes to convert the oil to derivatives of the oil and/or derivatives of the fatty acid contained in the oil.

An oil can be considered a marine oil if the oil includes at least 10%, 20%, 30%, 40%, 50%, 60%, 70%, 80%, 90%, 95% or 99% or more oil derived from a marine organism, where the oil derived from a marine organism can include processes to convert the oil to derivatives of the oil and/or derivatives of the fatty acid contained in the oil.

As used herein, the term "unsaturated fatty acid" refers to an unsaturated fatty acid or ester thereof, which can be an organic acid containing at least one carbon-carbon multiple bond, and the organic acid can be a carboxylic acid. In certain embodiments, a carbon-carbon multiple bond can be a double bond or triple bond. In certain embodiments, the carbon-carbon multiple bond can be in a group connected to the carbon atom of the carboxylic acid. When more than one carbon-carbon multiple bond is present, the carbon-carbon multiple bonds can be separated by zero or one or more methylene (—CH$_2$—) groups. Non-limiting examples, the unsaturated fatty acid or the ester thereof can comprise at least 10, at least 12, at least 14, at least 16, at least 18, or at least 20 carbon atoms. In some specific examples, the fatty acid or the ester thereof can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In other examples, the unsaturated fatty acid or the ester thereof can comprise a mixture of unsaturated fatty acids or the esters thereof having a range of carbon atoms. For example, the unsaturated fatty acid or the ester thereof can comprise from 10 to 40, from 12 to 38, from 14 to 36, from 16 to 34, from 18 to 32, or from 20 to 30 carbon atoms.

It will be understood by those of skill in the art that an polyunsaturated fatty acid can be an unsaturated fatty acid including more than one carbon—carbon multiple bonds. A polyunsaturated fatty acid can include two, three, four, five, six or more multiple carbon—carbon bonds. The carbon—carbon multiple bonds can be separated by zero or one or more methylene (—CH$_2$—) groups.

The polyunsaturated fatty acids can include omega-3 polyunsaturated fatty acids. As used herein, the term "omega-3 polyunsaturated fatty acid(s)" refers to a family of unsaturated fatty carboxylic acids that have in common a carbon-carbon bond in the n-3 position (i.e., the third bond from the methyl end of the molecule). Typically, they contain from about 16 to about 24 carbon atoms and from three to six carbon-carbon double bonds. Omega-3 polyunsaturated fatty acids can be found in nature, and these natural omega-3 polyunsaturated fatty acids frequently have all of their carbon-carbon double bonds in the cis-configuration.

Examples of omega-3 polyunsaturated fatty acids include, but are not limited to, 7,10,13-hexadecatrienoic acid (sometimes abbreviated as 16:3 (n-3)); 9,12,15-octadecatrienoic acid (alpha-linolenic acid (ALA), 18:3 (n-3)); 6,9,12,15-octadecatetraenoic acid (stearidonic acid (STD), 18:4 (n-3)); 11,14,17-eicosatrienoic acid (eicosatrienoic acid (ETE), 20:3 (n-3)); 8,11,14,17-eicosatetraenoic acid (eicosatetraenoic acid (ETA), 20:4 (n-3)); 5,8,11,14,17-eicosapentaenoic acid (eicosapentaenoic acid (EPA), (20:5 (n-3)); 7,10,13,16,19-docosapentaenoic acid (docosapentaenoic acid (DPA), 22:5 (n-3)); 4,7,10,13,16,19-docosahexaenoic acid (docosahexaenoic acid (DHA), 22:6 (n-3)); 9,12,15,18,21-tetracosapentaenoic acid (tetracosapentaenoic acid, 24:5 (n-3)); and 6,9,12,15,18,21-tetracosahcxacnoic acid (tetracosahexaenoic acid, 24:6 (n-3)).

As used herein, the term "omega-3 polyunsaturated fatty acid derivative(s)" refers to omega-3 polyunsaturated fatty acids that have been reacted with another compound or otherwise modified so that the omega-3 polyunsaturated fatty acid no longer contains a free carboxylic acid. Examples of omega-3 polyunsaturated fatty acid derivatives include salts, esters (such as alkyl esters including, but not limited to, methyl and ethyl esters) and glycerides of omega-3 polyunsaturated fatty acids.

It will be understood by those of skill in the art that an that the term "glyceride" means a glycerol molecule (i.e., $HOCH_2CHOHCH_2OH$) in which one, two or all three of the hydroxyls have been esterified with a carboxylic acid, e.g., an omega-3 polyunsaturated fatty acid. Thus, "triglyceride" refers to glycerides in which all three hydroxyls on the glycerol have been esterified with (the same or different) carboxylic acids. "Diglyceride" refers to glycerides in which only two of the hydroxyls on the glycerol have been esterified with (the same or different) carboxylic acids. "Monoglyceride" refers to glycerides in which only one hydroxyl on the glycerol has been esterified with a carboxylic acid.

Unsaturated fatty acids, and in particular, omega-3 fatty acids can be found in nature in the triglyceride form (a glycerol with three fatty acids attached). The natural triglyceride form as found in raw fish oil cannot be readily separated as it occurs into purified EPA/DHA-containing mixtures by ordinary means such as distillation or crystallization, because the fatty acids are non-uniformly distributed among the triglyceride molecules. There are very few, if any, single triglyceride molecules which are composed of either three EPA moieties or three DHA moieties. Typically, there is a DHA moiety, an EPA moiety, and another fatty acid moiety in a triglyceride molecule. So in order to purify fatty acids to increase the proportion of EPA, DHA, or the total fraction of omega-3's, it is necessary to hydrolyze the triglycerides to remove at least some fatty acids from the glycerol.

The triglycerides may be converted by any method known to one skilled in the art without limitation. For example, the triglycerides may be converted by lipase catalyzed esterification or lipase catalyzed acidolysis with ethyl or lauryl alcohol, which can selectively leave the highest amount of EPA and DHA bonded to glycerols and remove other components, leaving EPA and/or DHA as mono-or di-glycerides. The mono-and di-glycerides can then be separated into fractions with different EPA/DHA ratios, by methods familiar to those skilled in the art such as multiple stage vacuum distillation and/or fractional crystallization in urea. Advantageously, the purified EPA and DHA esters, after concentration, can be reattached to glycerol molecules using enzymatic reacylation to recreate glycerides which are otherwise identical to the original natural triglycerides, except that they are more concentrated in EPA and DIM combined, and they may also have a different ratio of EPA: DHA than the original source of the oil. In certain embodiments, at least 60% of the omega-3 fatty acids, and preferably 70% or more are converted to the triglyceride form in the reacylation process. The process may be successively repeated with addition of additional catalyst and/or enzyme and additional EPA and DHA until the desired specification proportions are met. About 60% of triglycerides can be made in the first pass of reacylation, with most of the remainder of the product being mono-and di-glycerides.

As used herein, the term "vitamin" refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (AND), Nicotinamide adenine clinucleotide phosphate (NADP), Coenzyme A (CoA), Coenzyme Q10 (CoQ10), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used herein, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof. Compounds containing these elements are also included in the term "mineral."

A variety of natural and artificial flavoring agents are available as additives to oils and can be, for example, an essence, an extract, a flavor oil, a nut oil, or combinations thereof.

A variety of natural and artificial coloring agents or colorants are available as additives to oils. The coloring agents may also include natural food colors and dyes suitable for food, drug and cosmetic applications. These coloring agents are known as FD & C dyes and lakes.

Sample of Oil and Possible Additives

In certain embodiments, a sample of oil that is to be tested can include an oil containing an unsaturated fatty acid. In certain embodiments, a sample of oil that is to be tested can include an oil containing an unsaturated fatty acid and one or more additives. The additives can be colorants, flavorings, antioxidants, vitamins, minerals, other essential oils, nutrients, preservatives, surfactants, dispersants, emulsifiers or other materials that are generally accepted as safe. In certain embodiments, each of the one or more additives can be present at levels of greater than about 1 ppm, about 2 ppm, about 5 ppm, about 10 ppm, about 50 ppm, about 100 ppm, about 500 ppm, about 1000 ppm, about 0.2%, about 0.5%, about 1%, 1.25%, about 1.5%, about 1.75%, about 2%, about 2.25%, about 2.5%, about 5%, or about 10% by weight/weight. In certain embodiments, each of the one or more additives has a molar absorptivity at 350 nm of at least 10 $M^{-1}cm^{-1}$, 50 $M^{-1}cm^{-1}$, 100 $M^{-1}cm^{-1}$, 500 $M^{-1}cm^{-1}$, 1000 $M^{-1}cm^{-1}$, 5000 $M^{-1}cm^{-1}$, 10,000 $M^{-1}cm^{-1}$, 20,000 $M^{-1}cm^{-1}$, 50,000 $M^{-1}cm^{-1}$, or 100,000 $M^{-1}cm^{-1}$. In certain embodiments, the additive is a flavoring. In certain embodiments, the flavoring is a lemon flavoring. In certain embodiments, the additive is a colorant.

In certain embodiments, the one or more additives in the sample of oil can react with p-anisidine to produce a reaction product. The percent of p-anisidine that reacts with the additives in the sample of oil is less than 10%, 5%, 2%, or 1% of the total amount of p-anisidine added to the sample of oil. In certain embodiments, the reaction product from the reaction of one or more additives with p-anisidine has a molar absorptivity at 350 nm of at least 500 $M^{-1}cm^{-1}$, 1000

$M^{-1}cm^{-1}$, 5000 $M^{-1}cm^{-1}$, 10,000 $M^{-1}cm^{-1}$, 20,000 $M^{-1}$, 50,000 $M^{-1}cm^{-1}$, or 100,000 $M^{-1}cm^{-1}$.

Preparation of Solutions

In certain embodiments, a standard p-anisidine solution can be prepared by adding a known amount of p-anisidine to a solvent. The amount of p-anisidine can be added by adding neat p-anisidine, either by measuring the mass or volume of the neat p-anisidine, or the amount of p-anisidine added can be from a volume of a solution of known concentration of p-anisidine. Mass or volume amounts of p-anisidine can be used to produce a solution with a known concentration, such as a stock p-anisidine solution. For example, a known mass of p-anisidine can be diluted with a solvent, to produce a solution that can be have a desired concentration or relative amount of p-anisidine. Sequential dilutions can be used starting with a known amount of p-anisidine to arrive at the desired concentration or relative amount of p-anisidine. For example, a stock p-anisidine solution with a known concentration of p-anisidine can be diluted to form a standard p-anisidine solution.

In certain embodiments, the amount of p-anisidine in a stock p-anisidine solution can be about 0.1 mg/mL, about 0.2 mg/mL, about 0.25, mg/mL, about 0.3 mg/mL, about 0.4 mg/mL, 0.5 mg/mL, about 0.6 mg/mL, about 0.7 mg/mL, about 0.75 mg/mL, about 0.8 mg/mL, about 0.9 mg/mL, about 1 mg/mL, about 2 mg/mL, about 2.5 mg/mL, about 3 mg/mL, about 4 mg/mL, about 5 mg/mL, about 6 mg/mL, about 7 mg/mL, about 8 mg/mL, about 9 mg/mL or about 10 mg/mL. In certain embodiments, the amount of p-anisidine in a standard p-anisidine solution can be about 0.1 mg/mL, about 0.2 mg/mL, about 0.25, mg/mL, about 0.3 mg/mL, about 0.4 mg/mL, 0.5 mg/mL, about 0.6 mg/mL, about 0.7 mg/mL, about 0.75 mg/mL, about 0.8 mg/mL, about 0.9 mg/mL, about 1 mg/mL, about 2 mg/mL, about 2.5 mg/mL, about 3 mg/mL, about 4 mg/mL, about 5 mg/mL, about 6 mg/mL, about 7 mg/mL, about 8 mg/mL, or about 9 mg/mL.

In certain embodiments, a sample solution is prepared by adding a certain amount of p-anisidine with a certain amount of a sample of oil to be tested. In certain embodiments, a solvent may be added. The sample solution can be allowed to stand for a certain time period, following the preparation of the sample solution, to allow the p-anisidine to react with some of the impurities in the sample of oil.

In certain embodiments, the sample solution is prepared so that the amount of p-anisidine in the sample solution before any p-anisidine reacts with the sample of oil can be the same as the amount of p-anisidine in a standard p-anisidine solution. In certain embodiments, the same amount of p-anisidine before any p-anisidine reacts with the sample of oil can be a same relative amount, such as a concentration. In certain embodiments, the same amount of p-anisidine before any p-anisidine reacts with the sample of oil can be an absolute amount, such as a mass or volume.

In certain embodiments, the amount of p-anisidine added to a sample of oil to be tested can be a mass or volume of p-anisidine. In certain embodiments, the amount of p-anisidine added to a sample of oil to be tested can be determined from a ratio of an amount of p-anisidine to an amount of the sample of oil.

In certain embodiments, the ratio of the amount of added p-anisidine to the amount of sample of oil to be tested can be a ratio of: a volume of p-anisidine to a volume of sample of oil; a volume of p-anisidine to a mass of sample of oil; a mass of p-anisidine to a volume of sample of oil; or a mass of p-anisidine to a mass of sample of oil. For example, ratios can be about 4:1 to 1:4, about 2:1 to 1:2, about 4:1 to 1:1, about 3:1 to 2:1, about 4:1, about 3:1, about 2.5:1, about 2:1, about 1.5:1, or about 1:1, where the ratio is volume to volume, mass to volume, volume to mass or mass to mass. The mass can be measured as grams (g) or milligrams (mg) and volume as liters (L) or milliliters (mL), and the ratios can be mL/mL, mg/mL, g/mL, L/mL, mL/mg, mg/mg, g/mg, L/mg, mg/L, g/L, ml/L, L/L, L/g, g/g, mL/g, or mg/g. In certain embodiments, the ratio of the amount of added p-anisidine to the amount of sample of oil to be tested can be a ratio of about 0.1 mg/mL to 10 mg/mL, about 0.5 mg/mL to 5 mg/mL, about 1 mg/mL to 3 mg/mL, about 2 mg/mL to 3 mg/mL, about 0.5 mg/mL about 1 mg/mL, about 2 mg/mL, about 2.5 mg/mL, about 3 mg/mL, or about 4 mg/mL.

In certain embodiments, the sample solution, following preparation, can stand for a time period to allow the p-anisidine to react with some of the impurities in the sample of oil. In certain embodiments, the time period can be at about 1 minute to 240 minutes, about 10 minutes to 180 minutes, about 60 minutes to 180 minutes, about 60 minutes to 120 minutes, about 1 minute, about 5 minutes, about 10 minutes, about 20 minutes, about 30 minutes, about 40 minutes, about 50 minutes, about 60 minutes, about 90 minutes, about 120 minutes, about 180 minutes, or about 240 minutes. In certain embodiments, the solvents used can be acids, such as acetic acid, formic acid, proprionic acid; aliphatic hydrocarbons, such as hexanes, heptanes; aromatic hydrocarbons such as benzene, toluene, xylenes; alcohols, such as methanol, ethanol, propanol, isopropanol, butanol; chlorinated hydrocarbons, such as chloroform, tetrachloroethylene, chlorobenzene; and mixtures of any of these solvents.

Measurement of the Amount of p-Anisidine

In certain embodiments, measurement of the amount of p-anisidine in the standard p-anisidine solution and the amount of p-anisidine remaining in the sample solution can be done by any method known to one of skill in the art that can quantitate the amount of p-anisidine in a solution. Non-limiting examples are liquid chromatography (LC), high performance liquid chromatography (HPLC), gas chromatography (GC), nuclear magnetic resonance spectroscopy (NMR), infrared spectroscopy (IR), or ultraviolet-visible spectroscopy (UV-VIS).

The amount of p-anisidine in the standard p-anisidine solution and the sample solution can be measured by any method known to one of skill in the art depending on the method and calculations used. The units, for example, can include peak area from an integrator, molar concentration (e.g., in mol/L, mmol/L, mmol/mL), mass concentration (e.g., in mg/mL, mg/L, g/L), or percent (e.g., in weight/weight, mass/mass, mass/volume, volume/mass or volume/volume).

In certain embodiments, the measurement of the amount of p-anisidine in the standard p-anisidine solution and the amount of p-anisidine remaining in the sample solution can be determined by HPLC. The HPLC method can use a variety of solvents. Non-limiting examples include water; acetonitrile; hydrocarbons, such as hexanes, heptanes, benzene or toluene; chlorinated hydrocarbons, such as chloroform or chloro benzene; alcohols, such as methanol, ethanol, propanol, or isopropanol; esters such as ethyl acetate or isopropyl acetate; ketones such as acetone and methyl ethyl ketone; ethers such as tetrahydrofuran and diethyl ether; acids, such as formic acid or acetic acid, or any other solvent that is known to one skilled in the art as useful as an HPLC solvent. In certain embodiments, mixtures of the above solvents can be used as well. Non-limiting examples can include mixtures of hydrocarbons and alcohols, acetonitrile and water, or isopropanol and hexane. In certain embodiments, the mixtures can be of two solvents or more than two solvents, such as three solvents, four solvents or five or more solvents.

In certain embodiments, the solvent system used in the HPLC method can be a mixture including isopropanol and hexane. In certain embodiments, the ratio of solvents can be about 5:95, about 10:90, about 20:80, about 30:70, about 40:60, or about 50:50, where the ratios are volume:volume. In certain embodiments, the solvent system used can be a 50:50 (volume:volume) mixture of isopropanol and hexane.

In certain embodiments, any HPLC column known to one skilled in the art that can sufficiently resolve the analytes of interest and allow for their detection and/or quantitation can be employed. In certain embodiments, the HPLC column can include a silica support onto which a polymeric chiral selector has been immobilized. In certain embodiments the chiral selector can be amylose tris (3,5-dimethylphenylearbamate). In certain embodiments, the silica support can be 20 μm silica support. In certain embodiments, the HPLC column can be a CHIRALPAK® IA column.

Determination of the Oxidation Level

In certain embodiments, determining the oxidation level of the sample of oil can be done by comparing an amount of p-anisidine remaining in the sample solution after the reaction of p-anisidine with the sample of oil, to an amount of p-anisidine in a standard p-anisidine solution, where the amount of p-anisidine in the sample solution before any p-anisidine reacts with the sample of oil can be or is the same as the amount of p-anisidine in the standard p-anisidine solution. The percent p-anisidine remaining can be calculated from the ratio of the amount of p-anisidine remaining in the sample solution over the amount of p-anisidine in the standard p-anisidine solution times one-hundred percent. The percent p-anisidine remaining can be an indication of the oxidation level of the sample of oil. The oxidation level can be an indication of whether the sample of oil is spoiled or rancid.

In certain embodiments, a method of determining an oxidation level of a sample of oil containing unsaturated fatty acid that is to be tested includes adding an amine, e.g., p-anisidine, to the sample of oil, where the p-anisidine can react with some of the impurities formed from oxidation of the sample of oil, and determining an amount of p-anisidine remaining after reaction of p-anisidine with the sample of oil, where the amount of p-anisidine remaining can provide an indication of the oxidation level of the sample of oil. In certain embodiments, the amount of p-anisidine remaining is calculated as a percentage, and denoted percent p-anisidine remaining. A certain oxidation level of the sample of oil can indicate that the oil is spoiled or rancid.

In certain embodiments, the oxidation level of a sample of oil, where the percent p-anisidine remaining is less than 50%, 75%, 80%, 85%, 86%, 87%, 88%, 89%, 90%, 91%, 92%, 93%, 94%, or 95%, can be an indication that the sample of oil is spoiled or rancid. In certain embodiments, the oxidation level of a sample of oil, where the percent p-anisidine remaining is more than 50%, 75%, 80%, 85%, 86%, 87%, 88%, 89%, 90%, 91%, 92%, 93%, 94%, or 95%, can be an indication that the sample of oil is not spoiled.

In certain embodiments, a method of determining an oxidation level of a sample of oil containing unsaturated fatty acid that is to be tested includes adding an amine, e.g., p-anisidine, to a sample of oil, where the p-anisidine can react with some of the impurities formed from oxidation of the sample of oil, and determining an amount of p-anisidine that reacted with the sample of oil, where the amount of p-anisidine that reacted can provide an indication of the oxidation level of the sample of oil. In certain embodiments, the amount of p-anisidine reacted is calculated as a percentage, and denoted percent p-anisidine reacted. A certain oxidation level of the sample of oil can indicate that the oil is spoiled or rancid.

In certain embodiments, the oxidation level of a sample of oil, where the percent p-anisidine reacted is greater than 90%, 85%, 80%, 75%, 70%, 60%, 50%, 40%, 30%, 20%, or 10%, can be an indication that the sample of oil is spoiled or rancid. In certain embodiments, the oxidation level of a sample of oil, where the percent p-anisidine reacted is less than 90%, 85%, 80%, 75%, 70%, 60%, 50%, 40%, 30%, 20%, or 10%, can be an indication that the sample of oil is not spoiled.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

HPLC Method

The following instrumentation and chromatography conditions were used for all the examples presented herein.

Instrumentation: HPLC system: Waters 2695 Separations Module, Waters 2487 Dual λ absorbance detector supported by Empower data acquisition system. HPLC column: CHIRALPAK® IA 4.6 mm×250 mm (Daicel Chemical Ltd) or equivalent.

Chromatography Conditions:
Column Temperature: 25° C.
Detection: UV at 254 nm
Injection Volume: 10 μL
Flow Rate: 1.0 mL/minute
Run Time: 10 minutes
Mobile Phase Hexane: 2-Propanol (50:50 (v/v))
Seal Wash: Mobile phase
Needle Wash Mobile phase Using these conditions, the retention of p-anisidine was approximately 4.7 minutes during a data acquisition time of 10 minutes.

Example 2

Determination of Linearity of p-Anisidine by HPLC

The following displays the linearity of the HPLC response to p-anisidine concentration for various standard p-anisidine solutions.

Standard p-Anisidine Solutions: A stock p-anisidine solution was prepared by accurately massing out an amount of p-anisidine (Aldrich item 188255, 99.8% purity) into a volumetric flask, and diluting to the fill line with acetic acid. Portions of this stock solution were further diluted with acetic acid to produce the standard p-anisidine solutions that were used in the linearity tests. The standard p-anisidine solutions had concentrations ranging from 0.1002 mg/mL to 0.5008 mg/mL. The standard p-anisidine solutions were then measured by HPLC according to the disclosed chromatography conditions of example 1, and the peak area by integrating the peak corresponding to the p-anisidine from the chromatogram was recorded. The results are displayed in Table 1, and show a linear HPLC response over the concentration range of p-anisidine measured.

TABLE 1

HPLC response to varying concentrations of p-Anisidine in a standard p-anisidine solution.

| p-Anisidine mg/mL | Peak Area | Results |
|---|---|---|
| 0.1002 | 857435 | Slope = 8486227 |
| 0.2003 | 1686027 | Intercept = −7063 |
| 0.3005 | 2530386 | Correlation Coefficient = 0.9999 |
| 0.4006 | 3381242 | |
| 0.5008 | 4259301 | |

Example 3 p-Anisidine Direct Measurement Test

A standard p-anisidine solution is prepared by adding a certain amount of p-anisidine in a solvent. The amount of p-anisidine in the standard p-anisidine solution is 0.25 mg in one mL of standard p-anisidine solution. The solvent that is used in the standard p-anisidine solution is acetic acid, or mixtures of acetic acid with another solvent.

A sample solution is prepared by adding a certain amount of a sample of oil with an amount of p-anisidine and diluting to a certain volume to obtain the desired concentration or relative amount of sample of oil and p-anisidine. The sample solution is prepared so that the desired concentration or relative amount of p-anisidine in the sample solution before any p-anisidine reacts with the sample of oil is the same as the amount of p-anisidine in the standard p-anisidine solution. The amount of the sample of oil in the sample solution is about 0.1 mL in one mL of sample solution, and the amount of p-anisidine in the sample solution is about 0.25 mg in one ml, of sample solution. The solvent used in the sample solution is a mixture of acetic acid and hexane. The sample solution, after being prepared, is allowed to react for a time period of about 180 minutes before the amount of p-anisidine remaining in the sample solution is measured, and the amount of p-anisidine in the standard solution is measured. The amount of p-anisidine remaining in the sample solution and the amount of p-anisidine in the standard p-anisidine solution are measured by the same method. Measuring the amount of p-anisidine remaining in the sample solution and the amount of p-anisidine in the standard p-anisidine solution is done by HPLC. The percent p-anisidine remaining is calculated by dividing the amount of p-anisidine remaining in the sample solution by the amount of p-anisidine in the standard p-anisidine solution and multiplying the quotient by 100 percent. The percent p-anisidine remaining of more than 70% indicates that the sample of oil is not spoiled.

Example 4 p-Anisidine Direct Measurement Test of Commercial Oil Samples

The following is an exemplary, non-limiting method of determining the level of p-anisidine remaining after reactions in a sample of marine oil.

Solution Preparation: A stock p-anisidine solution was prepared fresh for each experiment. The stock p-anisidine solution was prepared by combining p-anisidine (Aldrich item 188255, 99.8% purity) and acetic acid to a concentration of about 2.5 mg/mL, accurately determined. For example, 25 mg of p-anisidine were accurately massed out into a 10 mL volumetric flask, and diluted to volume with acetic acid, and the concentration in mg/mL of the stock solution was then calculated. The stock solution was used to prepare the standard p-anisidine solution and the sample solution. The same relative amount of stock p-anisidine solution was used in the preparation of the standard p-anisidine solution and sample solution.

To prepare the standard p-anisidine solution, the stock p-anisidine solution was diluted 10:1 with acetic acid, for example 1 mL the standard p-anisidine solution was diluted to 10 mL with acetic acid. The concentration of the standard p-anisidine solution, designated $C_{STD}$, was calculated from the concentration of the stock solution divided by 10, or about 0.25 mg/mL. The standard p-anisidine solution was then analyzed 6 times to provide an average of the response (peak area of the peak corresponding to p-anisidine in the chromatogram, designated $A_{STD}$) for a known concentration of p-anisidine, $C_{STD}$.

To prepare the sample solution, one part stock p-anisidine solution, one part sample of oil to be tested and 8 parts of hexane were mixed together. For example, 100 μL of the stock p-anisidine solution, 100 μL of a sample of oil to be tested, and 800 μL of hexane were pipetted into an HPLC vial and mixed, to make the sample solution. The sample solution was then analyzed 180 minutes after the sample solution was prepared by HPLC using the HPLC method of example 1. The response (peak area of the peak corresponding to p-anisidine in the sample solution chromatogram, designated $A_{SPL}$) for p-anisidine was recorded.

To determine the oxidation level of the sample of oil, the concentration of p-anisidine in the sample solution was compared to the concentration of p-anisidine in the standard p-anisidine solution. The concentration of p-anisidine in sample solution, designated $C_{SLP}$ was calculated by: $C_{SPL}=A_{SPL} \times C_{STD}/A_{STD}$, and percent p-anisidine remaining was calculated by: % p-anisidine remaining=100% $\times C_{SPL}$ $C_{SPL}/C_{STD}$.

Results: Table 2 presents the comparison of results from the spectrophotometric p-anisidine test in the prior art, and the p-anisidine direct measurement test by HPLC disclosed herein, for various samples of oils. The results demonstrate that there is little agreement between the results of spectrophotometric p-anisidine test and the results of the p-anisidine direct measurement test by HPLC, highlighting the need for a method that can more accurately determine the oxidation of oils containing materials that can interfere with the existing tests.

TABLE 2

Comparison of results from the spectrophotometric p-anisidine test (p-anisidine value, by method of AOCS Cd 18-90) and the test of Example 3 for various samples of oils.

| Sample of Oil | p-anisidine value | HPLC (% p-anisidine remaining) |
|---|---|---|
| Children's DHA | 18.1 | 97.0 |
| Ultimate Omega | 48.9 | 80.1 |
| Omega-3 | 66.8 | 72.2 |
| Arctic Cod Liver Oil | 32.7 | 88.0 |
| Complete Omega-3,6,9 | 48.6 | 80.1 |

Example 5

Measuring p-Anisidine Remaining in a Sample of Oil

The following is an exemplary, non-limiting method of measuring the amount of p-anisidine remaining in a sample of oil.

The level of oxidation of a sample of oil is to be determined by measuring the amount of p-anisidine remaining using HPLC. A stock p-anisidine solution is prepared by massing into a 10 mL volumetric flask, 0.0250 gm p-anisidine and diluting to the fill line of the volumetric flask with acetic acid. The concentration of the stock p-anisidine solution is 0.00250 gm/mL or 2.50 mg/mL. To make the standard p-anisidine solution, 1.00 mL of the stock p-anisidine solution is diluted to 10.00 mL with acetic acid. The concentration of the standard p-anisidine solution is given by dividing the concentration of the stock p-anisidine solution by the dilution amount, here being 10, to give $C_{STD}$=0.250 mg/mL. To make the sample solution, 1.00 mL of the stock p-anisidine solution, and 1.00 mL of a sample of oil to be tested are added to a 10.00 mL volumetric flask, and the flask is filled to the line with hexane and agitated. The mixture in the volumetric flask is allowed to react for a time period of 180 minutes.

After the time period, the sample solution and standard p-anisidine solution are each analyzed by HPLC using the method of example 1. The peak area in the chromatogram of the sample solution corresponding to p-anisidine is recorded as $A_{SPL}$=1987987. The peak area in the chromatogram of the standard p-anisidine solution corresponding to p-anisidine is recorded as $A_{STD}$=2114494. The concentration of p-anisidine in the sample solution is calculated by $C_{SPL}=A_{SPL}\times C_{STD}/A_{STD}$, which is (1987987×0.25)2114494=0.235 mg/mL. Knowing the molecular weight of p-anisidine of 123.15 g/mol, one can convert this result to a molar concentration by dividing by the molecular weight which gives 0.00191 mmol/mL. Calculation of the percent p-anisidine remaining is given by 100% ×$C_{SPL}/C_{STD}$=100% ×(0.235 mg/mL/0.25 mg/mL), which is 94% in this example. The sample of oil has an oxidation level corresponding to 94% p-anisidine remaining, which indicates that the sample of oil is not spoiled.

All of the references cited herein are incorporated by reference in their entirety. While the methods provided herein have been described with respect to the particular embodiments, it will be apparent to those skilled in the art that various changes and modifications can be made without departing from the spirit and scope as recited by the appended claims.

The embodiments described above are intended to be merely exemplary and those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method of determining oxidation of an oil comprising an unsaturated fatty acid, comprising the steps of: preparing a standard p-anisidine solution comprising an amount of p-anisidine; preparing a sample solution comprising an amount of p-anisidine and an amount of a sample of oil, wherein the sample of oil comprises an unsaturated fatty acid and wherein the amount of p-anisidine in the sample solution before any p-anisidine reacts with the sample of oil is the same as the amount of p-anisidine in the standard p-anisidine solution; measuring the amount of p-anisidine in the standard p-anisidine solution; measuring the amount of p-anisidine in the sample solution, wherein measuring the p-anisidine is done by one of chromatography, nuclear magnetic resonance spectroscopy (NMR), infrared spectroscopy (IR), and ultraviolet-visible spectroscopy (UV-VIS); and calculating a percent of p-anisidine remaining in the sample solution after the p-anisidine reacts with the sample of oil as compared with the standard p-anisidine solution, wherein the percent of p-anisidine remaining in the sample solution is an indication of oxidation of the sample of oil in the sample solution.

2. The method of claim 1, wherein the chromatography is HPLC.

3. The method of claim 1, wherein the percent p-anisidine remaining in the sample solution of less than 50%, 75%, 80%, 85%, 86%, 87%, 88%, 89%, 90%, 91%, 92%, 93%, 94%, or 95% is an indication of oxidation of the sample of oil in the sample solution.

4. The method of claim 1, wherein the amount of p-anisidine in the standard p-anisidine solution is from about 0.1 mg/mL to 1 mg/mL, from about 0.1 mg/mL to 0.5 mg/mL, or from about 0.2 mg/mL to 0.3 mg/mL.

5. The method of claim 1, wherein the amount of p-anisidine in the standard p-anisidine solution is about 0.2 mg/mL, about 0.25 mg/mL, about 0.3 mg/mL, about 0.4 mg/mL, or about 0.5 mg/mL.

6. The method of claim 1, wherein the amount of the sample of oil in the sample solution is from about 0.01 mL/mL to 0.2 mL/mL, from about 0.02 mL/mL to 0.1 mL/mL, or from about 0.05 mL/mL to 0.1 mL/mL.

7. The method of claim 1, wherein the amount of the sample of oil in the sample solution is about 0.2 mL/mL, about 0.1 mL/mL, about 0.05 mL/mL, or about 0.02 mL/mL.

8. The method of claim 1, wherein the measuring of the amount of p-anisidine in the sample solution is done more than 1 minute, 5 minutes, 10 minutes, 20 minutes, 30 minutes, 60 minutes, 120 minutes, 180 minutes or more than 180 minutes after preparing the sample solution.

9. The method of claim 1, wherein the measuring of the amount of p-anisidine produces a peak area, a mass, a weight, a concentration, a molar concentration, a mass concentration or weight concentration.

10. The method of claim 1, wherein the standard p-anisidine solution and sample solution further comprise acetic acid.

11. The method of claim 1, wherein the sample of oil comprises one or more oils selected from the group of vegetable oil, animal oil and marine oil.

12. The method of claim 11, where in the sample of oil comprises marine oil.

13. The method of claim 12, wherein the marine oil comprises a fish oil containing omega-3 fatty acids.

14. The method of claim 5, wherein the amount of p-anisidine in the standard p-anisidine solution is about 0.25 mg/mL.

15. The method of claim 7, wherein the amount of the sample of oil in the sample solution is about 0.1 mL/mL.

16. The method of claim 1, wherein the sample of oil comprises an additive.

17. The method of claim 16, wherein the additive has a molar absorptivity at 350 nm of at least 100 $M^{-1}cm^{-1}$.

18. The method of claim 16, wherein the additive is a coloring agent, a flavoring agent, a preserving agent, an antioxidant, or a vitamin.

19. The method of claim 16, wherein a reaction product of the additive with p-anisidine has a molar absorptivity at 350 nm of at least 1000 $M^{-1}cm^{-1}$.

20. The method of claim 1, wherein a ratio of the amount of p-anisidine in the sample solution to the amount of the sample of oil in the sample solution is from about 4:1 to 1:4, about 2:1 to 1:2, about 4:1 to 1:1, wherein the ratio is volume to volume, mass to volume, volume to mass, or mass to mass.

21. The method of claim 1, wherein a ratio of the amount of p-anisidine in the sample solution to the amount of the sample of oil in the sample solution is about 3:1 to 2:1, about 4:1, about 3:1, about 2.5:1, about 2:1, about 1.5:1 or about 1:1, wherein the ratio is volume to volume, mass to volume, volume to mass, or mass to mass.

22. The method of claim 21, where the ratio is 2.5:1, mass to volume.

\* \* \* \* \*